(12) United States Patent
Dewitt et al.

(10) Patent No.: US 11,998,424 B2
(45) Date of Patent: *Jun. 4, 2024

(54) PERFORATED BINDER FOR LAMINATED WOUND DRESSING

(71) Applicant: ConvaTec Technologies Inc., Las Vegas, NV (US)

(72) Inventors: David Dewitt, Lenoir City, TN (US); Jonathan Veal, Lenoir City, TN (US)

(73) Assignee: CONVATEC INC., Las Vegas, NV (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/583,505

(22) Filed: Jan. 25, 2022

(65) Prior Publication Data

US 2022/0168151 A1 Jun. 2, 2022

Related U.S. Application Data

(63) Continuation of application No. 16/261,332, filed on Jan. 29, 2019, now Pat. No. 11,241,339, which is a continuation of application No. 13/689,133, filed on Nov. 29, 2012, now Pat. No. 10,219,953.

(60) Provisional application No. 61/564,612, filed on Nov. 29, 2011.

(51) Int. Cl.
| | | |
|---|---|---|
| *A61F 13/00* | (2006.01) | |
| *A61F 13/02* | (2006.01) | |
| *A61F 13/0203* | (2024.01) | |
| *A61F 13/0206* | (2024.01) | |
| *A61F 13/0246* | (2024.01) | |

(52) U.S. Cl.
CPC .... *A61F 13/0206* (2013.01); *A61F 13/00063* (2013.01); *A61F 13/0203* (2013.01); *A61F 13/025* (2013.01); *A61F 13/0276* (2013.01); *A61F 2013/00246* (2013.01); *A61F 2013/00604* (2013.01); *A61F 2013/00634* (2013.01); *A61F 2013/0091* (2013.01); *A61F 2013/00936* (2013.01)

(58) Field of Classification Search
None
See application file for complete search history.

(56) References Cited

U.S. PATENT DOCUMENTS

| | | | |
|---|---|---|---|
| 4,099,342 A * | 7/1978 | Singh | B32B 27/34 36/44 |
| 11,058,807 B2 | 7/2021 | Weston | |
| 11,083,631 B2 | 8/2021 | Dunn et al. | |
| 11,090,409 B2 | 8/2021 | Zimnitsky et al. | |
| 11,241,339 B2 * | 2/2022 | Dewitt | A61F 13/0276 |

(Continued)

*Primary Examiner* — Kim M Lewis
(74) *Attorney, Agent, or Firm* — Taft Stettinius & Hollister LLP; Ryan O. White; Derek B. Lavender

(57) ABSTRACT

A method of manufacturing a laminated dressing that includes providing a lower layer having a fiber material that directly contacts a patient's skin and a wound area, providing an upper layer that has a foam or foam-like material that absorbs exudate and moisture, and binding the fiber-based lower layer and the foam-based upper layer with a binder layer comprising a binder material, the binder layer including a series of perforations. The perforations in the binder layer are formed by removing material from the binder layer with a pattern coated adhesive sheet prior to binding the fiber-based lower layer and the foam-based upper layer.

13 Claims, 3 Drawing Sheets

(56) References Cited

U.S. PATENT DOCUMENTS

2021/0338885 A1 11/2021 Zimnitsky et al.
2022/0001097 A1 1/2022 Weston
2022/0183894 A1 6/2022 Mumby et al.

* cited by examiner

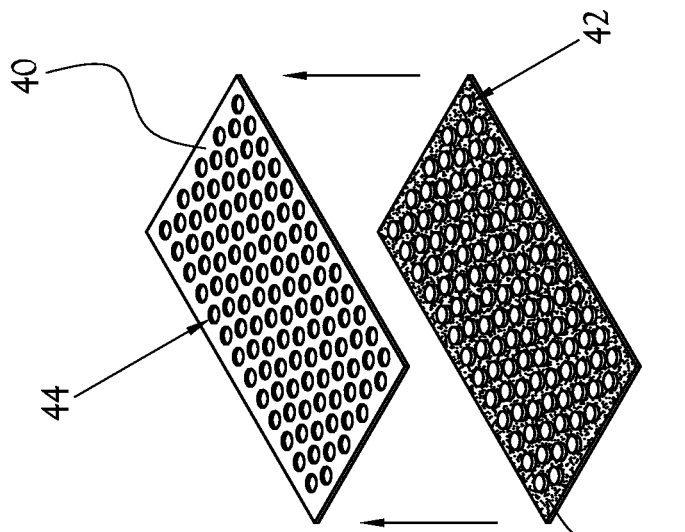
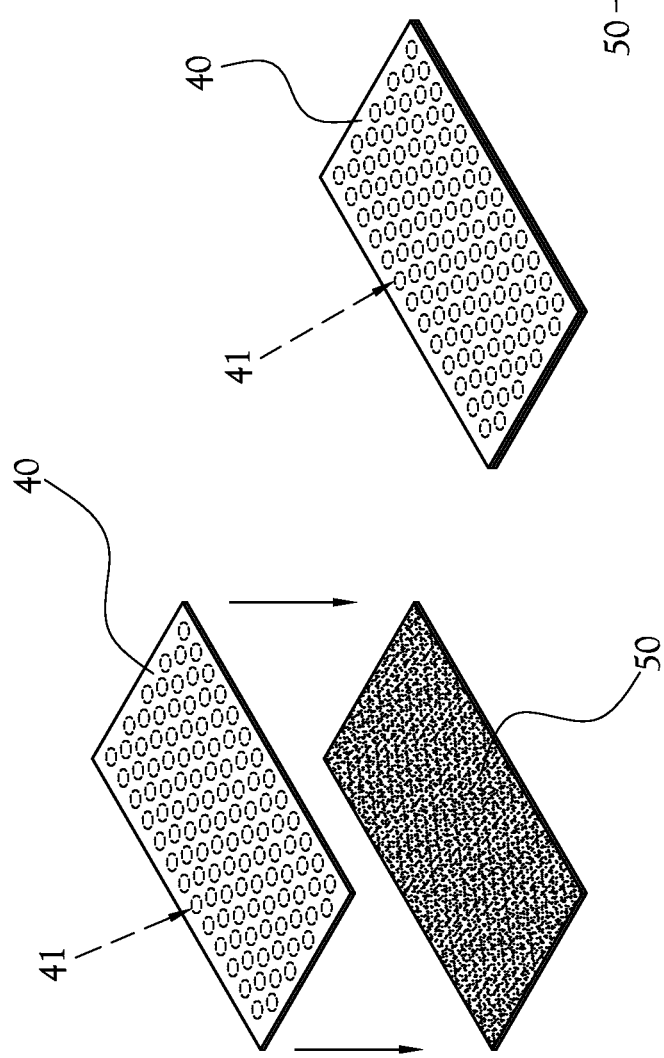

US 11,998,424 B2

PERFORATED BINDER FOR LAMINATED WOUND DRESSING

CROSS-REFERENCE

This Application is a continuation application of U.S. patent application Ser. No. 16/261,332, filed Jan. 29, 2019 which is a continuation application of U.S. patent application Ser. No. 13/689,133, filed Nov. 29, 2012, which claims priority to U.S. Provisional Patent Application No. 61/564,612, filed Nov. 29, 2011, each of which is incorporated in its entirety by reference herein.

STATEMENT REGARDING FEDERALLY SPONSORED RESEARCH OR DEVELOPMENT

Not Applicable

BACKGROUND OF THE INVENTION

Field of Invention

The present invention relates generally to wound dressings and particularly to a process of fabricating a perforated binder for a laminated dressing.

Description of the Related Art

Dressings have long been known in the art for protecting and treating wounds or areas of the epidermis that display irritation or visible infection. (Hereinafter, "wounds" is understood to encompass a wide variety of skin injuries and irregularities, including lacerations and puncture wounds as well as, e.g., rashes and eczema.) In recent decades, medical practitioners have come to understand the benefits of including an antimicrobial or anti-infection agent in the dressing to prevent infection of the wound during treatment.

Scarring is a natural part of the healing process. Scar tissue consists mainly of protein collagen formed during the skin's process of wound repair. With the exception of very minor lesions, skin wounds following accidents, disease or surgery all result in some degree of visible scarring. Where the scar tissue is large or in a prominent position on the body, it can be readily apparent to a casual observer and embarrassing or otherwise troubling for the scarred person. It is therefore desirable to have a wound dressing that can help minimize the appearance of scarring during the healing process.

An open wound is at a heightened risk of infection throughout the healing process. In particular, microorganisms such as bacteria and fungi will attempt to establish themselves in the moisture of the exudate extruded from the wound during the healing process. Medical practitioners have discovered that certain metals and metallic compounds, and in particular silver ions, when delivered to a wound, can kill microorganisms within and on the surface of the wound and thereby help fight infection.

It is therefore desirable to have a wound dressing that can supply an antimicrobial agent, such as silver ions, to a wound while also helping the wound to heal in a way to reduce the appearance of scar tissue.

BRIEF SUMMARY OF THE INVENTION

The present invention in some of its embodiments is directed toward a laminated dressing comprising three layers: a lower layer, comprising a fiber material, to directly contact a patient's skin and a wound area; an upper layer, comprising a foam or foam-like material to absorb exudate and moisture; and a middle layer or binder layer, comprising a binder material to bind the fiber-based lower layer and the foam-based upper layer. When the dressing is applied to a patient's skin and wound, the fiber-based lower layer is placed in direct contact with the patient's skin, generally covering the wound at least in part; the binder layer and foam-based upper layer sit on top of the fiber-based lower layer with respect to the patient's skin. Generally, during the manufacture or fabrication of a multi-layer or laminated dressing, the layers are brought together and heated in order to promote the formation of bonds—including, in various embodiments and depending on the materials used, physical and chemical bonds—between the multiple layers. The binder layer generally comprises a polymer-based fiber, such as a polyester or polyamide fiber, or a blend of such materials. Often, during the heating process, a polymer-based binder layer melts; when the melted binder layer re-solidifies at a later stage, the resulting binder layer is largely moisture-impermeable and therefore inhibits the transmigration of exudate or other moisture from the lower layer to the upper layer. The melting of the binder layer during the fabrication process results in a binder layer that inhibits the proper function of the laminated dressing, which aims to allow the foam-based upper layer draw moisture and exudate away from the wound and the lower layer in order to keep the wound dry and inhibit infection and irritation.

One way to limit the undesired results of the melting of the binder layer during the fabrication process is to cut perforations or holes in the binder layer before the binder layer is positioned between the lower layer and the upper layer. The pre-cut perforations ensure that, when the binder layer has melted, and then re-solidified after cooling, the re-solidified binder layer still includes perforations, through which moisture and exudate may pass from the lower layer to the upper layer.

However, when cutting perforations in a sheet of material for a binder layer, it is necessary to ensure that the cut-out material from the binder layer physically separates from the binder layer before the binder layer is positioned between the lower layer and the upper layer. In some example embodiments of the present general inventive concept, cut-out material from the binder layer is physically separated from the binder layer by adhering the cut-out material to a sheet covered with an adhesive material, such as a glue material. A binder layer is brought into contact with a sheet coated with a pattern of adhesive material (a "pattern-coated adhesive sheet"). As the binder layer is in contact with the pattern-coated adhesive sheet, a series of closed-loop cuts are made in the binder layer. The closed-loop cuts are made in such a way that the material enclosed by each closed loop is substantially physically separated from the remainder of the binder layer. Then the binder layer is moved away from the pattern-coated adhesive sheet, so that the binder layer and the pattern-coated adhesive sheet are no longer in contact. When the binder layer and the pattern-coated adhesive sheet are moved apart, the material enclosed in the closed-loop cuts—i.e., the cut waste fragments—are retained on the pattern-coated adhesive sheet, ensuring that the binder layer includes a series of cleared perforations.

In some embodiments of the present general inventive concept, a laminated dressing comprises a lower layer, comprising a fiber material, to directly contact a patient's skin and a wound area; an upper layer, comprising a foam or foam-like material to absorb exudate and moisture; and a binder layer, comprising a binder material to bind the fiber-based lower layer and the foam-based upper layer, the binder layer including a series of perforations. In some embodiments, said lower layer is fabricated from a non-woven, spunlaced polymer fabric. In some embodiments, said lower layer is fabricated from polyethylene fibers. In some embodiments, at least some of said polyethylene fibers are coated with silicone. In some embodiments, said lower layer is fabricated from regenerated cellulose fiber material. In some embodiments, some of said regenerated cellulose fiber material includes silicone. In some embodiments, said upper layer is fabricated from polyurethane. In some embodiments, said upper layer includes an antimicrobial agent. In some embodiments, said antimicrobial agent is inorganic. In some embodiments, said antimicrobial agent is metal-based. In some embodiments, said binder layer is fabricated from a polyester or polyamide material.

In some embodiments of the present general inventive concept, a method of fabricating a binder layer for a laminated dressing comprises bringing a binder layer into contact with a pattern-coated adhesive sheet; making a series of closed-loop cuts in the binder layer; and moving the binder layer away from the pattern-coated adhesive sheet, such that the binder layer and the pattern-coated adhesive sheet are no longer in contact, such that the material enclosed in the closed-loop cuts is retained on the pattern-coated adhesive sheet, whereby the binder layer includes a series of cleared perforations.

BRIEF DESCRIPTION OF THE SEVERAL VIEWS OF THE DRAWINGS

The above-mentioned and additional features of the invention will become more clearly understood from the following detailed description of the invention read together with the drawings in which:

FIG. 2A is a view of one stage of one embodiment of a process for removing cut material from a binder layer to form a perforated binder layer, showing an unperforated binder layer and a pattern-coated adhesive sheet;

FIG. 2B is a view of another stage of the example embodiment process shown in FIG. 2A, showing the binder layer in contact with the pattern-coated adhesive sheet;

FIG. 2C is a view of another stage of the example embodiment process shown in FIGS. 2A and 2B, showing the now-perforated binder layer moved away from the pattern-coated adhesive sheet.

DETAILED DESCRIPTION OF THE INVENTION

The present invention in some of its embodiments is directed toward a process of fabricating a perforated binder for a laminated dressing.

According to one embodiment of the present general inventive concept, illustrated generally at FIG. 1, a laminated dressing 10 comprises three layers: a lower layer 20, comprising a fiber material, to directly contact a patient's skin and a wound area; an upper layer 30, comprising a foam or foam-like material to absorb exudate and moisture; and a middle layer or binder layer 40 (hereinafter "binder layer"), comprising a binder material to bind the fiber-based lower layer 20 and the foam-based upper layer 30. When the dressing 10 is applied to a patient's skin and wound, the fiber-based lower layer 20 is placed in direct contact with the patient's skin, generally covering the wound at least in part; the binder layer 40 and foam-based upper layer 30 sit on top of the fiber-based lower layer 20 with respect to the patient's skin.

Figure 1:
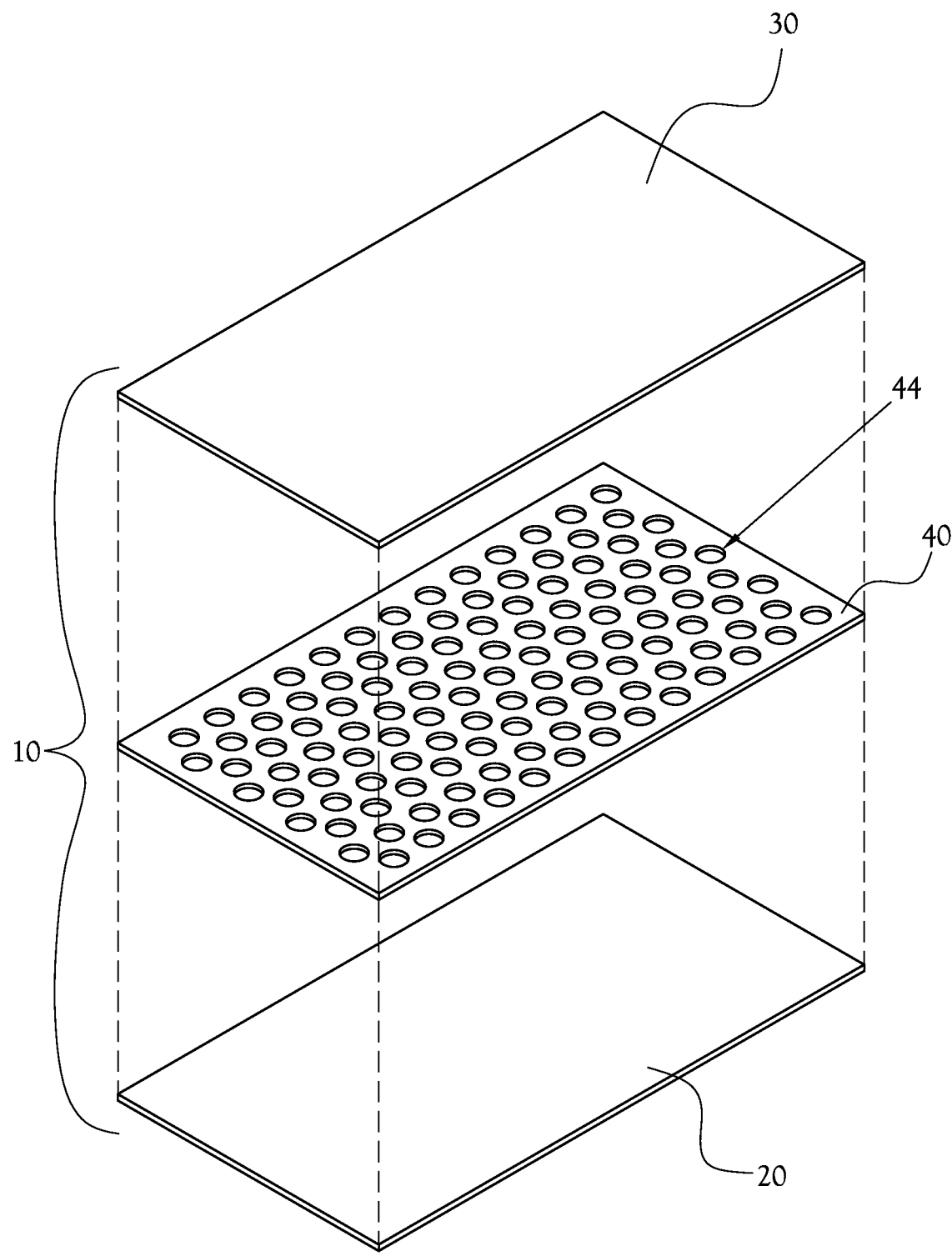
FIG. 1 is an exploded view of an example embodiment of the present invention.

Generally, during the manufacture or fabrication of a multi-layer or laminated dressing like the example embodiment dressing 10 illustrated in FIG. 1, the layers are brought together and heated in order to promote the formation of bonds—including, in various embodiments and depending on the materials used, physical and chemical bonds—between the multiple layers. The binder layer 40 generally comprises a polymer-based fiber, such as a polyester or polyamide fiber, or a blend of such materials. Often, during the heating process, a polymer-based binder layer 40 melts; when the melted binder layer 40 re-solidifies at a later stage, the resulting binder layer 40 is largely moisture-impermeable and therefore inhibits the transmigration of exudate or other moisture from the lower layer 20 to the upper layer 40. The melting of the binder layer 40 during the fabrication process results in a binder layer 40 that inhibits the proper function of the laminated dressing 10, which aims to allow the foam-based upper layer 30 draw moisture and exudate away from the wound and the lower layer 20 in order to keep the wound dry and inhibit infection and irritation.

One way to limit the counterproductive results of the melting of the binder layer 40 during the fabrication process is to cut perforations or holes 44 in the binder layer 40 before [[it]] the binder layer 40 is positioned between the lower layer 20 and the upper layer 30. Thus, for example, in the exploded view of an illustrated example embodiment, shown in FIG. 1, the binder layer 40 includes numerous perforations 44. The pre-cut perforations 44 (pre-cut in so far as the excised material is removed from the binder layer 40 before said binder layer 40 is inserted between the lower layer 20 and the upper layer 30) ensure that, when the binder layer 40 has melted, and then re-solidified after cooling, the re-solidified binder layer 40 still includes perforations, through which moisture and exudate may pass from the lower layer 20 to the upper layer 30.

However, when cutting holes 44 in a sheet of material for a binder layer, it is necessary to ensure that the cut-out material from the binder layer 40 physically separates from the binder layer 40 before the binder layer 40 is positioned between the lower layer 20 to the upper layer 30. In some example embodiments of the present general inventive concept, cut-out material from the binder layer 40 is physically separated from the binder layer 40 by adhering the cut-out material to a sheet covered with an adhesive material, such as a glue material. One example embodiment of a process according to one aspect of the present general inventive concept is illustrated generally in FIGS. 2A through 2C. In FIG. 2A, a binder layer 40 is brought into contact with a sheet 50 coated with a pattern of adhesive material (hereinafter, "pattern-coated adhesive sheet"). In FIG. 2B, the binder layer 40 is shown in contact with the pattern-coated adhesive sheet 50, with one face of the binder layer 40 substantially pressed against one face of the pattern-coated adhesive sheet 50. As the binder layer 40 is in contact with the pattern-coated adhesive sheet 50, a series of closed-loop cuts are made in the binder layer 40, generally along the phantom lines 41 shown on the binder layer 40 in FIGS. 2A and 2B. The closed-loop cuts are made in such a way that the material enclosed by each closed loop is substantially physically separated from the remainder of the binder layer 40. In FIG. 2C, the binder layer 40 is moved away from the pattern-coated adhesive sheet 50, so that the binder layer 40 and the pattern-coated adhesive sheet 50 are no longer in contact. When the binder layer 40 and the pattern-coated adhesive sheet 50 are moved apart, the material enclosed in the closed-loop cuts—i.e., the cut waste fragments 42—are retained on the pattern-coated adhesive sheet, ensuring that the binder layer 40 includes a series of cleared perforations 44.

Figure 3:
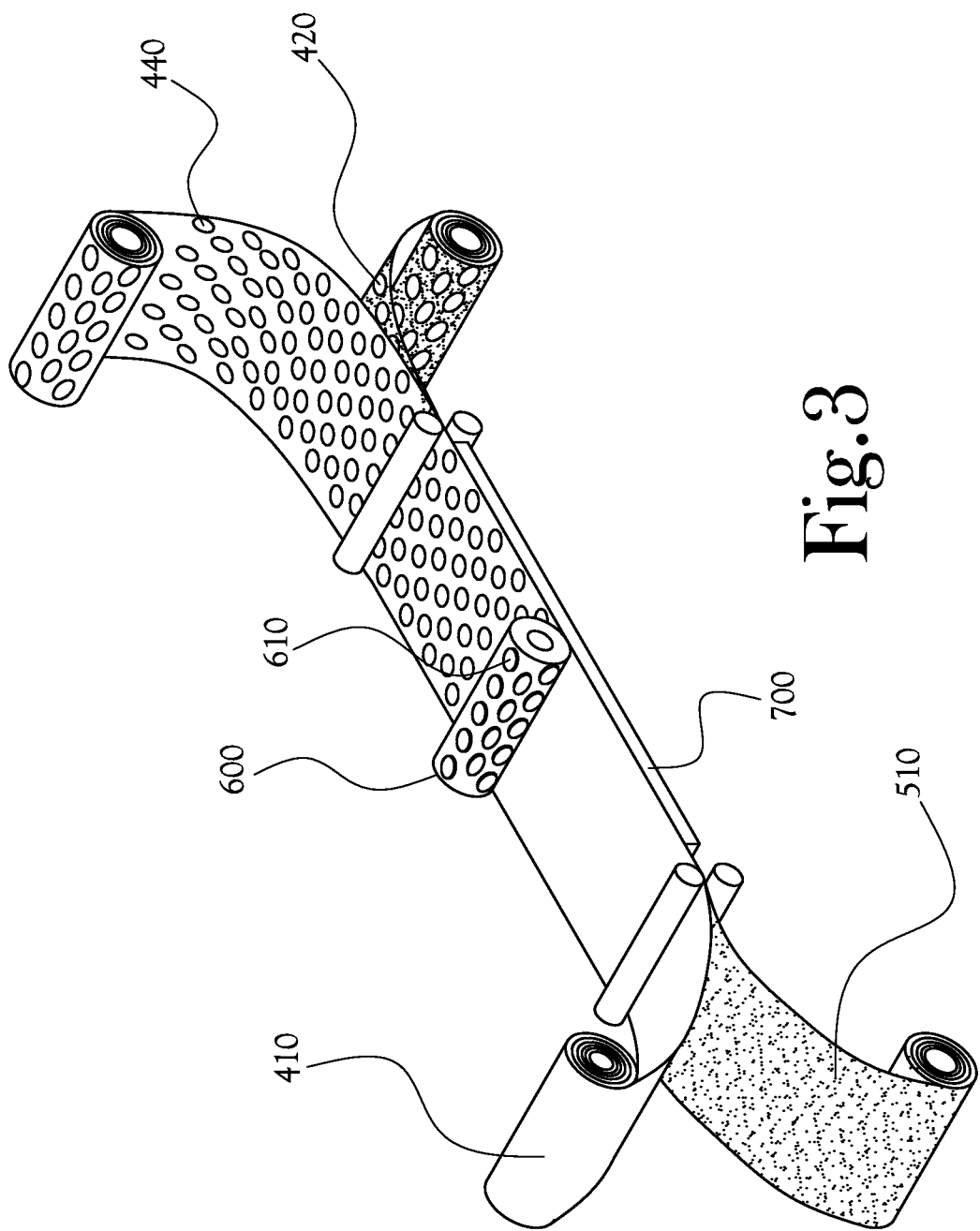
FIG. 3 is a perspective view of one embodiment of a process for form a perforated binder layer.

FIG. 3 illustrates one embodiment of a process for fabricating a perforated binder layer according to the present general inventive concept. In the illustrated example embodiment, a roll of binder layer 410 is unspooled and brought into contact with a roll of pattern-coated adhesive sheet 510, and the two rolls in contact are moved onto an assembly line 700. On the assembly line 700, a rolling cutter 600 is positioned above the roll of binder layer 410. The rolling cutter 600 includes a series of cutting punches 610, which make closed-loop cuts in the roll of binder layer 410. Then the binder layer 410 is moved away from the pattern-coated adhesive sheet 510, so that the binder layer 410 and the pattern-coated adhesive sheet 510 are no longer in contact. When the binder layer 410 and the pattern-coated adhesive sheet 510 are moved apart, the material enclosed in the closed-loop cuts—i.e., the cut waste fragments 420—are retained on the roll of pattern-coated adhesive sheet 510, ensuring that the binder layer 410 includes a series of cleared perforations 440.

In some embodiments, the lower layer comprises polyethylene fibers. In some embodiments, the lower layer comprises a porous mesh of polyethylene fibers. In some embodiments, the lower layer comprises a spun regenerated fiber material. In some embodiments, some or all of the fibers are coated with silicone. In some embodiments, the fibers are not coated with silicone.

In some embodiments, the foam-based upper layer comprises a foam fabricated from a hydrophilic polyurethane or comparable material. In some embodiments, the foam-based upper layer includes a metal-based antimicrobial agent that undergoes a controlled release when the binder layer comes into contact with moisture. In some embodiments, the upper layer includes an inorganic antimicrobial agent. In some embodiments, the upper layer does not include an inorganic antimicrobial agent.

When the dressing is used, the lower layer is applied directly to a patient's skin, covering or substantially covering the wound. The silicone in the lower layer interacts with the wound to minimize the appearance of scar tissue.

The dressing is either pre-wetted or applied dry to the wound. Moisture, either applied beforehand or from the wound exudate, travels through the porous fiber-based lower layer, through the binder layer, into the foam upper layer.

In some embodiments, moisture acts to release metal ions from controlled-release mechanisms, such as zeolites containing the metal ions, in the foam-based upper layer. The ions then travel within the moisture into the wound, where they act to kill bacteria and other infectious microorganisms and to prevent infections from gaining a foothold.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method of manufacturing a laminated dressing, comprising:
   providing a lower layer comprising a fiber material configured to directly contact a patient's skin and a wound area;
   providing an upper layer comprising a foam material configured to absorb exudate and moisture; and
   binding a fiber-based lower layer and a foam-based upper layer with a binder layer comprising a binder material, the binder layer including a series of perforations;
   wherein the perforations in the binder layer are formed by removing material from the binder layer with a pattern coated adhesive sheet prior to binding the fiber-based lower layer and the foam-based upper layer.

2. The method of claim 1 wherein said lower layer is fabricated from a non-woven, spunlaced polymer fabric.

3. The method of claim 1 wherein said lower layer is fabricated from polyethylene fibers.

4. The method of claim 3 wherein some of said polyethylene fibers are coated with silicone.

5. The method of claim 1 wherein said lower layer is fabricated from regenerated cellulose fiber material.

6. The method of claim 5 wherein some of said regenerated cellulose fiber material includes silicone.

7. The method of claim 1 wherein said upper layer is fabricated from polyurethane.

8. The method of claim 1 wherein said upper layer includes an antimicrobial agent.

9. The method of claim 8 wherein said antimicrobial agent is inorganic.

10. The method of claim 8 wherein said antimicrobial agent is metal-based.

11. The method of claim 1 wherein said binder layer is fabricated from a polyester or polyamide material.

12. A method of fabricating a laminated dressing comprising:
    bringing a binder layer into contact with a pattern-coated adhesive sheet;
    making a series of closed-loop cuts in the binder layer; and
    moving the binder layer away from the pattern-coated adhesive sheet to remove portions of the pattern coated adhesive with the binder layer to form a series of cleared perforations in the pattern-coated adhesive.

13. The method of claim 12 wherein said binder layer is fabricated from a polyester or polyamide material.

* * * * *